Figure 1:
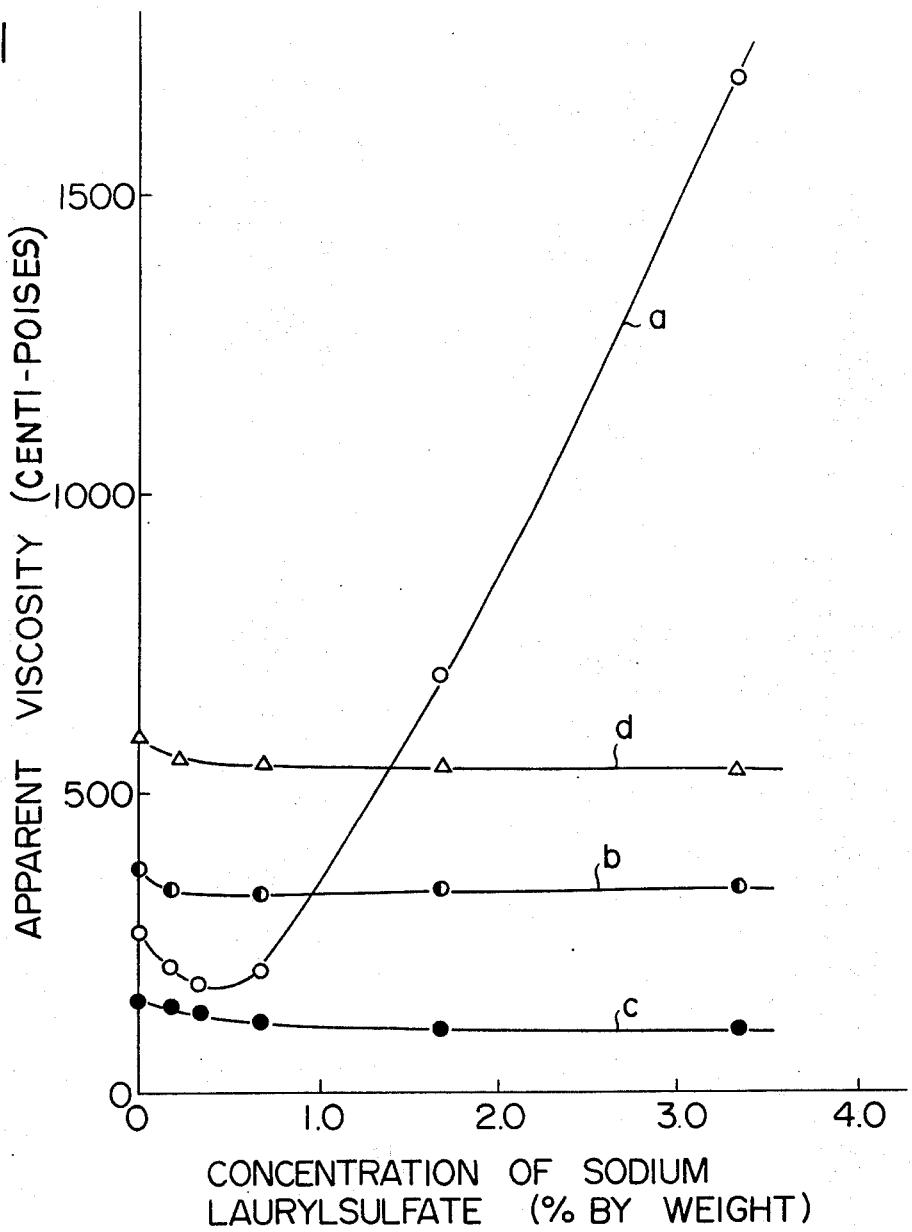

United States Patent [19]
Hashimoto et al.

[11] 3,963,832
[45] June 15, 1976

[54] LIQUID OR PASTY DENTIFRICE AND PROCESS FOR ITS PREPARATION

[75] Inventors: Shigeru Hashimoto, Suita; Eizi Ninomiya, Tokyo; Junko Kuroda, Kyoto, all of Japan

[73] Assignees: Teijin Limited; Sunstar Dentifrice Co., Ltd., both of Osaka, Japan

[22] Filed: July 24, 1975

[21] Appl. No.: 598,846

Related U.S. Application Data

[63] Continuation-in-part of Ser. No. 435,184, Jan. 21, 1974, abandoned.

[30] Foreign Application Priority Data

Jan. 24, 1973   Japan................................. 48-9447

[52] U.S. Cl.................................... 424/56; 424/49; 424/58
[51] Int. Cl.² ...................... A61K 7/16; A61K 7/26
[58] Field of Search ................................ 424/49–58

[56] References Cited

UNITED STATES PATENTS

| | | | |
|---|---|---|---|
| 3,506,757 | 4/1970 | Salzmann | 424/52 |
| 3,551,559 | 12/1970 | Miles | 424/49 |

OTHER PUBLICATIONS

Chem. Abst. 69, No. 64652w (1968).
Chem. Abst. 71, No. 11737n (1969).

*Primary Examiner*—Shep K. Rose
*Attorney, Agent, or Firm*—Sherman & Shalloway

[57] ABSTRACT

A liquid or pasty putrefaction resistant thixotropic gel dentifrice that is stable against phase separation of solid abrasive dentifrice particle ingredients which consists of 0.3 to 2% by weight of a polysaccharide having a number average molecular weight of not less than 100,000 and the molecule of said polysaccharide containing D-glucose, D-mannose, D-galactose and D-glucuronic acid in the molar ratio of about 3:3:1:2.

2 Claims, 2 Drawing Figures

LIQUID OR PASTY DENTIFRICE AND PROCESS FOR ITS PREPARATION

This application is a continuation-in-part application of application Ser. No. 435,184 filed Jan. 21, 1974, now abandoned.

This invention relates to a liquid or pasty dentifrice having various properties which have been desired but have been unable to stand together in a single dentifrice, and to a process for preparing such a liquid or pasty dentifrice. More specifically, this invention relates to a liquid or pasty dentifrice comprising, uniformly incorporated therein, preferably in a proportion of 0.3 to 2 parts by weight per 100 parts by weight of the dentifrice, a thickening and suspending agent consisting of a polysaccharide having a number average molecular weight ($\overline{Mn}$) of not less than 100,000, the molecule of the polysaccharide containing D-glucose, D-mannose, D-galactose and D-glucuronic acid in the approximate molar ratio of 3:3:1:2.

It has been known that by utilizing the ability of a xanthomonas hydrophilic colloid to form a stabilized suspension of an abrasive in a liquid dentifrice, the colloid is incorporated in the liquid dentifrice to provide a stable, homogeneous, pourable liquid dentifrice (U.S. Pat. No. 3,506,757 patented Apr. 14, 1970). It has also been known that by utilizing the ability of the xanthomonas hydrophilic colloid to improve the pourability of a pasty dentifrice from a container and its dispersibility in the mouth as compared with a conventional thickening and suspending agent such as Irish moss or a sodium salt of carboxymethyl cellulose, the colloid is incorporated into the pasty dentifrice to provide an improved pasty dentifrice (British Pat. application No. 4081/71 filed Feb. 5, 1971; corresponding to German OLS No. 2,204,670 laid open on Aug. 10, 1972).

The xanthomonas hydrophilic colloid described above is a polysaccharide reported, for example, in U.S. Pat. Nos. 3,067,038, 3,391,061, 3,427,226, 3,516,983, and 3,519,434. This polysaccharide can be prepared by cultivating Xanthomonas compestris in a medium containing a saccharide, and separating the resulting product from the culture medium. The above-cited U.S. Pat. No. 3,506,737 discloses the use of a polysaccharide the molecule of which contains mannose, glucose, potassium glucuronate and acetyl in the approximate molar ratio of 2:1:1:1 as the xanthomonas hydrophilic colloid to be incorporated in the liquid dentifrice. Furthermore, the German OLS No. 2,204,670 discloses the use of a partially acetylized polysaccharide, the molecule of which contains D-glucose, D-mannose and D-glucuric acid in the molar ratio of 2.8:3.0:2.0.

We have now found that a liquid or pasty dentifrice comprising another bacterial polysaccharide the molecule of which contains D-glucose, D-mannose, D-galactose and D-glucuronic acid in the approximate molar ratio of 3:3:1:2 has improved properties and superior resistance to putrefaction as compared with the conventional liquid or pasty dentifrice containing a xanthomonas hydrophilic colloid.

It has also been found that the dentifrice of this invention containing the above bacterial polysaccharide has unique thixotropy whereby the dentifrice easily flows under a low pressure, and sensitively loses its flowability upon removal of the pressure, and that when the dentifrice is included in a container and extruded onto a tooth brush in use, it can be extruded with good flowability by a light extruding pressure, and as soon as it leaves the extrusion opening, it loses its flowability and retains the shape as extruded. Furthermore, the dentifrice of this invention also has self-shape-maintaining properties (the property to retain a given shape as its own characteristic) and viscoelastic properties upon removal of an external pressure. For example, when the dentifrice is extruded from the container as mentioned above, it can easily break off without remaining adhered to the outlet of the container. Furthermore, the above dentifrice of this invention has very good dispersibility and bubbling properties in the mouth, and disperse and retain the conventional dentifrice ingredients stably in the dentifrice, and does not lead itself to phase separation of the ingredients. Furthermore, it has been found that the bacterial polysaccharide used in this invention has a unique interaction with a detergent or surfacd active agent used as one of the conventional dentifrice ingredients. Since the apparent viscosity and the viscoelastic property of the dentifrice can be very easily controlled by utilizing this unique interaction, the use of a small amount of the bacterial polysaccharide can lead to the adjustment of the apparent viscosity of the liquid or pasty dentifrice to the desired value over a wide range.

Accordingly, an object of this invention is to provide an improved liquid or pasty dentifrice having superior properties and superior resistance to putrefaction compared with the conventional dentifrice containing a polysaccharide.

Another object of this invention is to provide a process for preparing such a dentifrice.

Many other objects of this invention along with its advantages will become more apparent from the following description.

The bacterial polysaccharide, the molecule of which contains D-glucose, D-mannose, D-galactose, and D-glucuronic acid in the approximate molar ratio of 3:3:1:2, is known, and can be obtained by cultivating a known bacteria Bacillus polymyxa (No. 271 strain: FERM-P. No. 1824; the Microorganism Research Institute, Agency of Industrial Science & Technology, Japan) in a culture medium containing a saccharide, and collecting the polysaccharide produced in the medium. The physical and chemical properties of this polysaccharide and the method of its cultivation are described, for example, in Japanese Patent Publication No. 7600/67 and Die Angewandte Makromolekular Chemie., Band 6 (1969), pages 179–185.

There has previously been no attempt to incorporate this bacterial polysaccharide in a liquid or pasty dentifrice, and there has neither been any disclosure or suggestion that the resultant dentifrice has all of the above-mentioned improved properties. The following properties of the above known bacterial polysaccharide are known. Refined polysaccharide, which is called No. 271 gum, is colorless, tasteless, and odorless, and it was soluble in water to give a clear solution, but insoluble in organic solvents such as alcohols, ethers, acetone, and chloroform. The pure polysaccharide is composed of D-glucose, D-mannose, D-galactose, and D-glucoronic acid in a molar ratio of 3:3:1:2, as determined from the results of column-chromatographic analysis of the acid hydrolyzate.

The polysaccharide, as used herein and the appended claims, denotes such a pure polysaccharide and a crude polysaccharide composed predominantly of such a pure polysaccharide. An aqueous solution of the polysaccharide is also known to have high viscosity comparable with that of gum guar, and the viscosity is enhanced in the presence of acids, salts and sugars. The polysaccharide has a high water hold capacity, and forms a viscoelastic gel from its ethanol solution in a concentration of 40 percent.

Nevertheless, the above unique thixotropy, self-shape-maintaining properties, stabilized dispersibility, the unique interaction with a detergent or surface active agent, and the resistance to putrefaction, etc. which are essential requirements for the present invention have not been known heretofore.

The bacterial polysaccharide utilized in this invention can be produced by methods known per se. For example, it can be prepared by cultivating *Bacillus polymyxa* in a culture medium containing at least one of such saccharides as glucose, mannose, galactose, lactose, maltose, glycerol, mannitol, sucrose, fructose and xylose, removing the cells and other solids from the culture liquid, adding a precipitant to the resulting liquid phase to precipitate crude polysaccharide, separating and collecting the precipitate, and if desired, purifying the precipitate.

The culture medium may further contain a nitrogen source and minerals.

Examples of the nitrogen source are peptone, urea, corn steep liquor, yeast extract, and ammonium sulfate.

Examples of the minerals are magnesium sulfate, monobasic potassium phosphate, calcium carbonate, and manganese sulfate.

The cultivation can be performed under aerobic conditions at a temperature of from about 20°C to about 37°C, preferably from about 25°C to about 33°C with the pH of the culture medium being maintained at from 4.5 to 7.5, preferably from 5 to 7. Usually, the cultivating time is about 40 hours to 3 days.

As the precipitant, there can be utilized an alcohol, an ether, acetone, chloroform, etc. Specific examples include methyl alcohol, isopropyl alcohol, acetone, chloroform, and an aqueous solution of a quaternary ammonium salt.

At this time, a subsidiary precipitant, for example, potassium chloride, can be used conjointly.

The crude polysaccharide obtained was dissolved in a suitable amount of water and precipitated by the precipitant described above to purify it. This dissolving-precipitating-separating cycle can be repeated a desired number of times. The polysaccharide obtained can be dried by vacuum drying or other means, and pulverized.

According to this invention, a liquid or pasty dentifrice can be provided by cultivating *Bacillus polymyxa* (No. 271 strain) in a culture medium containing a saccharide as described above, collecting the polysaccharide (meant to be both in the pure and crude forms) which has thus been produced in the culture medium and which has a number average molecular weight ($\overline{Mn}$) of not less than 100,000, the molecule of said polysaccharide containing D-glucose, D-mannose, D-galactose and D-glucuronic acid in the approximate molar ratio of 3:3:1:2, and blending the resulting polysaccharide with a liquid or pasty dentifrice as a thickening and suspending agent in an amount of 0.3 to 2 parts by weight per 100 parts by weight of the dentifrice.

The polysaccharide used in this invention has a number average molecular weight ($\overline{Mn}$) of not less than 100,000, usually 100,000 to 5,000,000, preferably 300,000 to 3,000,000.

The number average molecular weight ($\overline{Mn}$) is determined by measuring the viscosities of solutions of the above polysaccharide of the desalted type in various concentrations in a 1% aqueous solution of sodium hydroxide, obtaining the intrinsic viscosity [$\eta$] by an extrapolating method, and substituting the intrinsic viscosity value for the Staudinger's equation below.

$$[\eta] = Km \cdot \overline{Mn}^\alpha$$

wherein
$Km = 3.08 \times 10^{-5}$, and
$\alpha = 0.85$, which were used by Misaki et al. about a polysaccharide produced by *Bacillus Polymyxa var. lactoviscosus*.

The polysaccharide in the present invention need not altogether be of the desalted type, but may be in the form of an alkali metal salt such as a sodium or potassium salt, or an alkaline earth metal salt such as a calcium salt. Accordingly, the above polysaccharide used in this invention as a thickening and suspending agent includes not only a desalted type but also an alkali metal or alkaline earth metal salt type.

The amount of the polysaccharide used in this invention as a thickening and suspending agent is preferably 0.3 to 2 parts by weight, more preferably about 0.5 to about 1 part by weight.

The dentifrice of this invention contains conventional well-known dentifrice ingredients such as humectants, detergents or surface active agents, flavoring materials, sweetening agents, abrasives, coloring materials, anti-caries agents, fungicidal or bacteriocidal agents, or water. The use of the coloring materials, anti-caries agents, and fungicidal or bacteriocidal agents may be omitted. The amounts of these conventional dentifrice ingredients may be changed within the conventional ranges. Most commonly, in the case of a liquid dentifrice, a formulation consisting of 25 to 45% by weight of water, 20 to 35% of weight of abrasives, 20 to 35% by weight of humectants, 0.5 to 2% by weight of detergents or surface active agents, 0.3 to 2% by weight of the polysaccharide used in this invention, and the remainder being the other dentifrice ingredients can be utilized. In the case of a pasty dentifrice, the utilizable formulation consists of 25 to 35% by weight of water, 35 to 50% by weight of abrasives, 15 to 30% by weight of humectants, 0.5 to 2% by weight of detergents or surface active agents, 0.3 to 2% by weight of the polysaccharide used in this invention, and the remainder being the other dentifrice ingredients.

A part of the polysaccharide used as a thickening and suspending agent can be replaced by a known thickening and suspending agent for dentifrice. The suitable amount of such a known thickening and suspending agent is not more than about 1.4 times the weight of the polysaccharide, preferably equal to the weight of the polysaccharide or less.

Examples of the conventional known thickening and suspending agents are carboxymethyl cellulose, its alkali metal salts, carrageenan, sodium alginate, hydroxyethyl cellulose, methyl cellulose tragacanth gum, locast beans gum, and tamarind seed-polysaccharide.

Examples of the humectants include glycerol, sorbitol, maltitol, glucose, propylene glycol, polyethylene glycol and sodium pyrrolidone carboxylate.

Examples of the abrasives are dicalcium phosphate dihydrate, calcium pyrophosphate, anhydrous dicalcium phosphate, insoluble sodium metaphosphate, hydrated alumina, calcium carbonate, magnesium carbonate, magnesium oxide, and finely powdered silica.

Examples of the detergents or surface active agents are sodium lauryl sulfate, sodium N-lauroyl sarcosinate, α-olefin sulfonate, sodium 2-hydroxyalkyl sulfate, sodium laurylether sulfate, sodium coconut monoglyceride sulfate, sodium coconut monoglyceride sulfonate, a sodium salt of a monoester of lauroylethanolamide sulfosuccinic acid, polyoxyethylene fatty acid esters such as polyoxyethylene sorbitan monolaurate, polyoxyethylene sorbitan monopalmitate, polyoxyethylene sorbitan monostearate, or polyoxyethylene stearate having a degree of polymerization of at least 25, and a polyoxyethylene polyoxypropylene block copolymer.

Examples of the flavoring materials are peppermint oil, spearmint oil, sassafras oil, clove oil, sage oil, Eucalyptus oil, marjoram oil, lemon oil, cinnamon oil, orange oil, and sodium methyl salicylate.

The sweetening agents may, for example, be sodium saccharate.

Examples of the coloring materials, anti-caries agents, and fungicidal or bacteriocidal agents are sodium fluoride, tin fluoride, hexachlorophene, and sodium monofluorophosphate.

An example of changes in apparent viscosity by the interaction between the polysaccharide used in this invention and surface active agents is shown in FIG. 1 along with an example of changes in apparent viscosity of carboxymethyl cellulose, carrageenan and Xanthomonas hydrophilic colloid (conventional thickening and suspending agents) in the presence of surface active agents.

Figure 2:
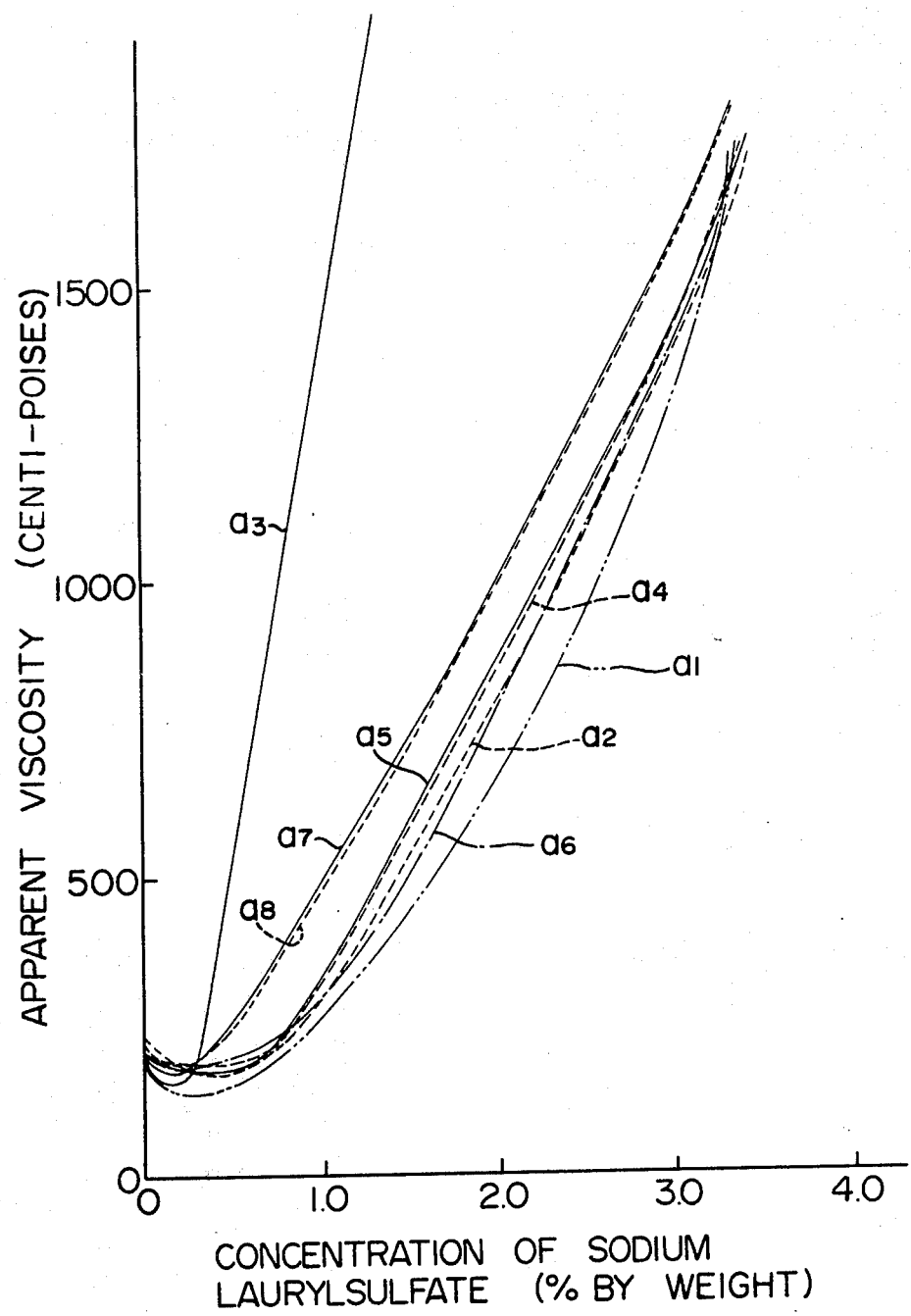

The invention will become better understood when viewed with the accompanying drawings wherein:

FIG. 1 graphically illustrates the interaction of a polysaccharide and sodium lauryl sulfate as the surfact active agent in accordance with the present invention, and FIG. 2 graphically illustrates the interaction of polysaccharide and other surface active agents in accordance with the present invention.

In FIG. 1, the curve $a$ shows the changes in the apparent viscosity (centipoises) of a 1% aqueous solution of the polysaccharide ($\overline{Mn}$ = 1,500,000) which has been measured at 25°C. using a Brookfield viscometer with No. 2 rotor at a speed of 20 rpm, with changes in the concentration (% by weight) of sodium laurylsulfate as a surface active agent. Curves $b$ and $c$ show similar changes in apparent viscosity with regard to carboxymethyl cellulose and carrageenan. Curve $d$ shows similar changes in apparent viscosity with regard to Xanthomonas hydrophilic colloid.

As seen in FIG. 2, wherein curves $a_1$, $a_2$, $a_3$, $a_4$, $a_5$, $a_6$, $a_7$ and $a_8$ were obtained by following the same procedures as the above except that sodium N-lauroyl sarcosinate ($a_1$), sodium coconut monoglyceride sulfate ($a_2$), α-olefin sulfonate ($a_3$), sodium 2-hydroxy alkyl sulfate ($a_4$), sodium laurylether sulfate ($a_5$), sodium coconut monoglyceride sulfonate ($a_6$), polyoxyethylene sorbitan monolaurate ($a_7$) and polyoxyethylene sorbitan monopalmitate ($a_8$) were each used in place of the above sodium laurylsulfate as a surface active agent, there is provided a unique interaction between the polysaccharide and other surface active compounds.

From FIGS. 1 and 2, it is seen that in the present invention, a unique interaction between the polysaccharide and a surface active agent occurs. This fact has to do with the unique thixotropy of the polysaccharide used in the dentifrice of this invention, and contributes to an improvement in the extrudability of the dentifrice of this invention.

The dentifrice of this invention has superior resistance to putrefaction as compared with the case of using Xanthomonas hydrophilic colloid.

A 1% aqueous solution of each of the polysaccharide used in this invention and xanthane gum was blended with each of the antiseptics shown in Table 1 in the amount indicated. Each of the blends obtained was allowed to stand at about 40°C. for two weeks, and then the putrefying smell and bubbles formed as a result of putrefaction were observed. The results are shown in Table 1.

Table 1

| | Antiseptic | Amount of antiseptic (% by weight) | | | | | |
| --- | --- | --- | --- | --- | --- | --- | --- |
| | | 0 | 0.025 | 0.05 | 0.1 | 0.5 | 1 |
| Polysaccharide of this invention | butyl p-oxybenzoate | + | — | — | — | — | — |
| | methyl p-oxybenzoate | + | — | — | — | — | — |
| | ethyl p-oxybenzoate | + | — | — | — | — | — |
| | potassium salt of sorbic acid | + | — | — | — | — | — |
| | hexachlorophene | + | — | — | — | — | — |
| Xanthane gum | butyl p-oxybenzoate | +++ | +++ | +++ | +++ | + | + |
| | methyl p-oxybenzoate | +++ | +++ | +++ | +++ | + | + |
| | ethyl p-oxybenzoate | +++ | +++ | +++ | +++ | + | + |
| | potassium salt of sorbic acid | +++ | +++ | +++ | +++ | +++ | +++ |
| | hexachlorophene | +++ | ++ | + | — | — | — |

The evaluations were made on the following scale.

+++ considerable putrefying smell, and evolution of much gas

++ putrefying smell, evolution of gas to a lesser extent than +++

+ putrefying smell and evolution of gas observed slightly

− neither putrefying smell nor evolution of gas observed.

These results demonstrate clearly that the polysaccharide used in this invention exhibits very good resistance to putrefaction.

The dentifrice of this invention has superior stability to heat, stability with lapse of time and resistance to putrefaction, in addition to superior extrudability, dispersibility of solid dentifrice ingredients, shape retention after extrusion, smoothness of the surface of the extrudate, dispersibility in the mouth, break-off from the opening of the container at the time of extrusion foamability in the mouth, and flavor.

The dentifrice of this invention is especially preferred as a liquid dentifrice capable of being poured in the form of liquid from a container such as a plastic bottle, or glass bottle, or a liquid dentifrice capable of being easily poured from a pump-type container (a container of the type wherein the liquid within is sucked up by operating a pump provided at the stopcock) or from an aerosol container.

If a conventional thickening and suspending agent such as carboxymethyl cellulose is blended in the case of a lotion-like liquid dentifrice, the addition of a sufficient amount of a dentifrice abrasive results in the reduction of the viscosity of the resulting dentifrice. Accordingly, the amount of the thickening and suspending agent cannot but be reduced. As a result, the precipitation of a dentifrice abrasive is observed, and when the dentifrice thus obtained is poured onto a toothbrush, it cannot maintain its shape on the brush, but falls down among the brush hairs.

In the case of a liquid dentifrice filled in a pump-type container, if a conventional thickening agent such as carboxymethyl cellulose is used, the resulting liquid dentifrice could be used at a viscosity of about 150 poises. However, when the viscosity rises to 200 poises, it becomes completely useless. In contrast, the dentifrice of this invention, even when having a viscosity of about 200 poises, can be fully used.

When a pasty dentifrice in accordance with this invention is filled in a tube having a diameter in excess of that of a usual tube for a pasty dentifrice (about 5 mm to about 10 mm), it sometimes happens that the surface smoothness of the extrudate is somewhat impaired. This disadvantage can be easily overcome by adding about 1% by weight of amorphous ultrafine anhydrous silicon dioxide and/or about 0.5% by weight of a non-inonic surface active agent.

The following Examples and Comparative Examples illustrate the liquid or pasty dentifrice of this invention. Unless otherwise specified, all parts are parts by weight and each polysaccharide is obtained by cultivating *Bacillus polymyxa* (FERM-P. No. 1824) in the prescribed saccharide-containing culture medium.

Example 1 (liquid dentifrice)
| | |
|---|---|
| Calcium carbonate | 30.0 parts |
| Polysaccharide (product in a sucrose culture medium, average molecular weight about 1,500,000) | 1.0 part |
| Glycerol | 30.0 parts |
| Water | 36.36 parts |
| Sodium laurylsulfate | 1.5 parts |
| Sodium saccharate | 0.1 part |
| Flavor | 1.0 part |
| Fungicide | 0.04 part |

The above polysaccharide, fungicide and sodium saccharate were pre-mixed, and with stirring, glycerol was gradually added, followed by addition of water. By thorough mixing, the mixture became viscous. Calcium carbonate was added to this mixture with stirring, and thoroughly dispersed. The flavor and sodium laurylsulfate were then added, and the mixture was stirred in vacuo to form a uniform composition as a liquid dentifrice.

Example 2 (liquid dentifrice)
| | |
|---|---|
| di-calcium phosphate dihydrate | 30 parts |
| Polysaccharide (product in a sucrose culture medium, average molecular weight about 1,500,000) | 1.0 parts |
| Glycerol | 30.0 parts |
| Water | 36.36 parts |
| Sodium laurylsulfate | 1.5 parts |
| Sodium saccharate | 0.1 part |
| Flavor | 1.0 part |
| Fungicide | 0.04 part |

In accordance with the above formulation, a liquid dentifrice was prepared in the same way as in Example 1.

Example 3 (liquid dentifrice)
| | |
|---|---|
| di-calcium phosphate dihydrate | 30.0 parts |
| Polysaccharide (the product in a glucose culture medium, average molecular weight about 500,000) | 0.3 part |
| Carboxymethyl cellulose | 0.2 part |
| Glycerol | 30.0 parts |
| Water | 36.36 parts |
| Sodium laurylsulfate | 1.5 parts |
| Sodium saccharate | 0.1 part |
| Flavor | 1.0 part |
| Fungicide | 0.04 |

In accordance with the above formulation, a liquid dentifrice was prepared in the same way as in Example 1.

Example 4 (pasty dentifrice)
| | |
|---|---|
| di-calcium phosphate dihydrate | 45.0 parts |
| Polysaccharide (the product in a sucrose culture medium, average molecular weight about 2,000,000) | 0.5 part |
| Carboxymethyl cellulose | 0.5 part |
| Glycerol | 10.0 parts |
| Sorbitol | 10.0 parts |
| Water | 30.86 parts |
| Sodium laurylsulfate | 1.5 parts |
| Polyoxyethylene polyoxypropylene block copolymer (80% of the polyoxyethylene portion, molecular weight about 8800) | 0.5 parts |
| Sodium saccharate | 0.1 part |
| Flavor | 1.0 part |
| Fungicide | 0.04 part |

In accordance with the above formulation, a pasty dentifrice was prepared in the same way as Example 1.

For comparison, a pasty dentifrice (Comparative Example 1) was prepared in the same way except that Xanthomonas hydrophilic colloid was used instead of the polysaccharide in the above formulation.

The resistance to putrefaction of this pasty dentifrice was compared with that of the dentifrice obtained in Example 4. Specifically, each of the pasty dentifrices was packed in a tube, and the changes with the passage of time in an atmosphere at about 40°C. were observed. It was found that the dentifrice of this invention did not give off bad smell nor evolve gas even after a lapse of 3 months, whereas the dentifrice of Comparative Example 1 gave off bad smell after a lapse of 2 weeks.

Example 5 (pasty dentifrice)
| | |
|---|---|
| di-calcium phospate di-hydrate | 45.0 parts |
| Polysaccharide | |

Example 5 (pasty dentifrice)

| | |
|---|---|
| (the product in a glucose culture medium, average molecular weight about 2,500,000) | 0.35 part |
| Carboxymethyl cellulose | 0.5 part |
| Glycerol | 10.0 parts |
| Sorbitol | 10.0 parts |
| Water | 30.86 parts |
| Sodium laurylsulfate | 1.5 parts |
| Polyoxyethylene monostearate (DP about 40) | 0.5 part |
| Sodium saccharate | 0.1 part |
| Flavor | 1.0 part |
| Fungicide | 0.04 part |

In accordance with the above formulation, a pasty dentifrice was prepared in the same way as in Example 1.

Example 6 (pasty dentifrice)

| | |
|---|---|
| di-calcium phosphate dihydrate | 45.0 parts |
| Polysaccharide (the product in a glucose culture medium, average molecular weight about 1,000,000) | 0.5 part |
| Carboxymethyl cellulose | 0.5 part |
| Glycerol | 10.0 parts |
| Sorbitol | 10.0 parts |
| Water | 30.36 parts |
| Sodium laurylsulfate | 1.5 parts |
| Anhydrous silicon dioxide | 1.0 part |
| Sodium saccharate | 0.1 part |
| Flavor | 1.0 part |
| Fungicide | 0.04 part |

In accordance with the above formulation, a pasty dentifrice was prepared in the same way as in Example 1.

Example 7 (pasty dentifrice)

| | |
|---|---|
| di-calcium phosphate dihydrate | 45.0 parts |
| Polysaccharide (the product in a glucose culture medium, average molecular weight about 1,500,000) | 0.5 part |
| Sodium alginate | 0.5 part |
| Water | 30.36 parts |
| Sodium laurylsulfate | 1.5 parts |
| Anhydrous silicon dioxide | 1.0 part |
| Sodium saccharate | 0.1 part |
| Flavor | 1.0 part |
| Fungicide | 0.04 part |

In accordance with the above formulation, a pasty dentifrice was prepared in the same way as in Example 1.

Example 8 (pasty dentifrice)

| | |
|---|---|
| Dicalcium phosphate dihydrate | 45.0 parts |
| Polysaccharide (the product in a glucose culture medium, average molecular weight about 1,000,000) | 0.6 part |
| Carrageenan | 0.5 part |
| Sorbitol | 20.0 parts |
| Sodium laurylsulfate | 1.5 parts |
| Anhydrous silicon dioxide | 1.0 part |
| Sodium saccharide | 0.1 part |
| Flavor | 1.0 part |
| Fungicide | 0.04 part |
| Water | 30.36 parts |

In accordance with the above formulation, a pasty dentifrice was prepared in the same way as in Example 1.

Example 9 (liquid dentifrice)

| | |
|---|---|
| Dicalcium phosphate dihydrate | 30.0 parts |
| Polysaccharide (product in a sucrose culture medium, average molecular weight about 1,500,000) | 1.0 parts |
| Glycerol | 15.0 parts |
| Propyrene glycol | 15.0 parts |
| Sodium N-lauroyl sarcosinate | 1.5 parts |
| Water | 36.36 parts |
| Sodium saccharate | 0.1 part |
| Flavor | 1.0 parts |
| Fungicide | 0.04 part |

Example 10 (liquid dentifrice)

| | |
|---|---|
| Dicalcium phosphate dihydrate | 30.0 parts |
| Polysaccharide | 1.0 parts |
| Glycerol | 15.0 parts |
| Sorbitol | 15.0 parts |
| Water | 36.36 parts |
| Sodium coconut monoglyceride sulfate | 1.5 parts |
| Sodium saccharate | 0.1 part |
| Flavor | 1.0 parts |
| Fungicide | 0.04 part |

Example 11 (liquid dentifrice)

| | |
|---|---|
| Calcium carbonate | 30.0 parts |
| Polysaccharide | 1.0 parts |
| Glycerol | 15.0 parts |
| Sorbitol | 10.0 parts |
| Propyrene glycol | 5.0 parts |
| Water | 36.36 parts |
| α-olefin sulfonate | 1.5 parts |
| Sodium saccharate | 0.1 part |
| Flavor | 1.0 parts |
| Fungicide | 0.04 part |

COMPARATIVE EXAMPLES 2 TO 4

Liquid dentifrices were prepared in the same way as in Example 1 using the same formulations in Examples 2, 3 and 4 respectively except that the polysaccharide was replaced by the same amount of carboxymethyl cellulose.

The tackiness of the liquid dentifrice obtained in Examples 1 to 3 was compared with that of the liquid dentifrices obtained in Comparative Examples 2 to 4. As a method of comparing the tackinesses, the number of pushings of a pump which was required for the dentifrice to come out from a pump-type container was determined. The results are shown in Table 2.

Table 2

| Samples | Viscosity (centipoises) | Number of times |
|---|---|---|
| Example 1 | 380 | 6 |
| Example 2 | 400 | 6 |
| Example 3 | 390 | 7 |
| Comparative Example 2 | 350 | 25 |
| Comparative Example 3 | 390 | 28 |
| Comparative Example 4 | 390 | 27 |

The pump-type container is adapted to suck up the contents by the difference between the atmospheric pressure and the pressure within the cylinder in accordance with the same principle as a pump for taking up water from a well. When the contents are extruded by a smaller number of pushings of the pump, the flowability of the contents in the container and in a narrow slit is better. This means that the paste flows by a slight difference in pressure (external force). It is advantageous to the consumer that the contents can be extruded more easily when the number of pushings of the pump is smaller.

As is seen from Table 2, the dentifrices using the polysaccharide of this invention exhibit very characteristic tackiness at the same viscosity (centipoises). In the case of Comparative Examples, the contents can be extruded by more than 20 pushings, but the manner of pouring is extremely unsatisfactory. In contrast, the contents are extruded very smoothly in accordance with this invention.

Various thickening and suspending agents were compared using a 50% aqueous solution of glycerol as a model, and the results are shown in Table 3.

When the conventional thickening and suspending agents are used, quite the same tendency as in the above Comparative Example can be observed.

Table 3

| Thickening and suspending agent | Concentration (wt. %) | Temperature (°C.) | Viscosity (centipoises) | Number of pushings |
| --- | --- | --- | --- | --- |
| Carboxymethyl cellulose (of low viscosity, DP about 150) | 2 | 25 | 58 | 6 |
| | 2 | 13 | 90 | 6 |
| | 3 | 25 | 192 | 6 |
| | 4 | 25 | 442 | 23** |
| Carboxymethyl cellulose (of medium viscosity, DP about 200) | 2 | 25 | 112 | 7 |
| | 2 | 12 | 184 | 9 |
| Carboxymethyl cellulose (of high viscosity, DP ca. 600) | 2 | 25 | 224 | 10* |
| | 2 | 9 | 380 | 23** |
| | 3 | 25 | 922 | 100** |
| Carrageenan | 2 | 25 | 220 | 7 |
| | 2 | 12 | 374 | 26** |
| Sodium alginate | 2 | 25 | 146 | 6 |
| | 2 | 12 | 240 | 10* |
| Polysaccharide (of low viscosity, molecular weight about 500,000, culture medium glucose) | 2 | 25 | 220 | 6 |
| | 2 | 11.5 | 454 | 10 |
| Polysaccharide (of high viscosity, molecular weight about 1.5 million, culture medium glucose) | 2 | 25 | 400 | 8 |
| | 2 | 25 | 483 | 6 |
| | SLS2% *** | | | |
| Xanthomonas hydrophilic colloid | 2 | 25 | 210 | 50 |

The viscosities were measured by a Brookfield viscometer with a rotor No. 7. The contents flow out when the number of pushings is as indicated in Table 3, but the contents do not come out smoothly (*). The asterisk ** indicates that the contents flow out with more difficulty than in the case of *. The asterisk *** indicates that SLS stands for sodium laurylsulfate.

EXAMPLES 12–17

(Liquid Dentifrice)

There were prepared respective liquid dentifrices being quite the same as the dentifrice of Example 1 except that the abrasive, humectant and surface active agent were replaced respctively by what were shown in Table 4.

The number of pushings of a pump which was required for the dentifrice to come out of a pump-type container was determined. In either case, the liquid dentifrice was 6 in the number of pushing times.

Table 4

| Ex. No. | Abrasives (kind and parts) | Humectants (kind and parts) | | Surface active agents (kind and parts |
| --- | --- | --- | --- | --- |
| 12 | calcium pyrophosphate 30.0 | Glycerol and 15.0 | moltitol 15.0 | Sodium 2-hydroxy alkyl sulfate 1.5 |
| 13 | anhydrous dicalcium phosphate 30.0 | Glycerol and 15.0 | glucose 15.0 | Sodium laurylether sulfate 1.5 |
| 14 | insoluble sodium metaphosphate 30.0 | Glycerol and 25.0 | polyethylene glycol 5.0 | Sodium coconut monoglyceride sulfonate 1.5 |
| 15 | hydrated alumina 30.0 | Glycerol + 25.0 | sodium pyrrolidone carboxylate 5.0 | polyoxyethylene sorbitan monolaurate 1.5 |
| 16 | magnesium carbonate 30.0 | Glycerol 30.0 | | polyoxythylene sorbitane monopalmitate 1.5 |
| 17 | magnesium oxide 30.0 | Glycerol 30.0 | | sodium lauryl sulfate 1.5 |

What is claimed is:

1. A liquid putrefaction resistant thixotropic gel dentifrice that is stable against phase separation of solid abrasive dentifrice particle ingredients which essentially consists of:

25 to 35% by weight of water, 20 to 35% by weight of humectants, selected from the group consisting of glycerol, sorbitol, maltitol, glucose, propylene glycol, polyethylene glycol and sodium pyrrolidone carboxylate, 0.5 to 2% by weight of a member selected from the group consisting of sodium lauryl sulfate, sodium N-lauroyl sarcosinate, α-olefin sulfonate, sodium 2-hydroxyalkyl sulfate, sodium laurylether sulfate, sodium coconut monoglyceride sulfate, sodium coconut monoglyceride sulfonate, a sodium salt of a monoester of lauroylethanolamide sulfosuccinic acid, polyoxyethylene fatty acid esters such as polyoxyethylene sorbitan monopalmitate, polyoxyethylene sorbitan monostearate, or polyoxyethylene stearate having a degree of polymerization of at least 25, and a polyoxyethylene polyoxypropylene block copolymer, 0.3 to 2% by weight of a polysaccharide having a number average molecular weight of not less than 100,000 and the molecule of said polysaccharide containing D-glucose, D-mannose, D-galactose and D-glucuronic acid in the molar ratio of about 3:3:1:2, and 20 to 35% by weight of solid particles of abrasives, selected from the group consisting of dicalcium phosphate dihydrate, calcium pyrophosphate, anhydrous dicalcium phosphate, insoluble sodium methaphosphate, hydrated alumina, calcium carbonate, magnesium carbonate, magnesium oxide, and silica, whereby said thixotropic gel dentifrice flows easily under low pressure and with good flowability, and when extruded loses its flowability upon removal of extrusion pressure while retaining the shape as extruded.

2. A pasty putrefaction resistant thixotropic gel dentifrice that is stable against phase separation of solid abrasive dentifrice particle ingredients which essentially consists of:

25 to 35% by weight of water, 15 to 30% by weight of humectants, selected from the group consisting of glycerol, sorbitol, maltitol, glucose, propylene glycol, polyethylene glycol and sodium pyrrolidone carboxylate, 0.5 to 2% by weight of a member selected from the group consisting of sodium lauryl sulfate, sodium N-lauroyl sarcosinate, α-olefin sulfonate, sodium 2-hydroxyalkyl sulfate, sodium laurylether sulfate, sodium coconut monoglyceride sulfate, sodium coconut monoglyceride sulfonate, a sodium salt of a monoester of lauroylethanolamide sulfosuccinic acid, polyoxyethylene fatty acid esters such as polyoxyethylene sorbitan monopalmitate, polyoxyethylene sorbitan monostearate, or polyoxyethylene stearate having a degree of polymerization of at least 25, and a polyoxyethylene polyoxypropylene block copolymer, 0.3 to 2% by weight of a polysaccharide having a number average molecular weight of not less than 100,000 and the molecule of said polysaccharide containing D-glucose, D-mannose, D-galactose and D-glucuronic acid in the molar ratio of about 3:3:1:2, and 35 to 50% by weight of solid particles of abrasives, selected from the group consisting of dicalcium phosphate dihydrate, calcium pyrophosphate, anhydrous dicalcium phosphate, insoluble sodium metaphosphate, hydrated alumina, calcium carbonate, magnesium carbonate, magnesium oxide, and silica, whereby said thixotropic gel dentifrice flows easily under low pressure and with good flowability, and when extruded loses its flowability upon removal of extrusion pressure while retaining the shape as extruded.

* * * * *